United States Patent
North

(10) Patent No.: US 9,259,570 B2
(45) Date of Patent: Feb. 16, 2016

(54) ELECTRODE HAVING ERECTABLE LEAD

(71) Applicant: Richard B. North, Baltimore, MD (US)

(72) Inventor: Richard B. North, Baltimore, MD (US)

( * ) Notice: Subject to any disclaimer, the term of this patent is extended or adjusted under 35 U.S.C. 154(b) by 0 days.

(21) Appl. No.: 14/218,129

(22) Filed: Mar. 18, 2014

(65) Prior Publication Data

US 2014/0257446 A1   Sep. 11, 2014

Related U.S. Application Data

(62) Division of application No. 12/804,560, filed on Jul. 23, 2010, now Pat. No. 8,676,346.

(60) Provisional application No. 61/228,399, filed on Jul. 24, 2009.

(51) Int. Cl.
  *A61N 1/05* (2006.01)

(52) U.S. Cl.
  CPC .................... *A61N 1/0553* (2013.01)

(58) Field of Classification Search
  CPC .................................... A61N 1/0553
  See application file for complete search history.

(56) References Cited

U.S. PATENT DOCUMENTS

| | | | |
|---|---|---|---|
| 4,313,448 A | 2/1982 | Stokes | |
| 4,765,341 A | 8/1988 | Mower et al. | |
| 5,404,876 A | 4/1995 | DiSabito et al. | |
| 6,066,165 A | 5/2000 | Racz | |
| 6,445,958 B1 | 9/2002 | Machek et al. | |
| 6,522,932 B1 | 2/2003 | Kuzma et al. | |
| 6,546,293 B2 | 4/2003 | Errico et al. | |
| 6,671,554 B2 | 12/2003 | Gibson et al. | |
| 7,107,104 B2 | 9/2006 | Keravel et al. | |
| 7,251,529 B2 | 7/2007 | Greenwood-Van Meerveld | |
| 2005/0015128 A1 | 1/2005 | Rezai et al. | |
| 2005/0070919 A1 | 3/2005 | Lieberman | |
| 2005/0288760 A1 | 12/2005 | Machado et al. | |
| 2009/0060978 A1 | 3/2009 | Bluecher | |
| 2009/0099439 A1 | 4/2009 | Barolat | |

FOREIGN PATENT DOCUMENTS

WO   WO 2005/028025   3/2005

*Primary Examiner* — Joseph Dietrich
(74) *Attorney, Agent, or Firm* — Whiteford, Taylor & Preston, LLP; Gregory M. Stone

(57) ABSTRACT

Disclosed is an electrode, such as an SCS paddle electrode, having a lead attached thereto along an interior portion of the electrode. The lead and electrode are configured such that the lead may be positioned generally coplanar with a top surface of the electrode, and may likewise be erected from such coplanar orientation up and away from the top surface of the electrode. Thus, the lead can maintain the typical configuration of emerging from the back end of the electrode, but because at least portions of the lead are not permanently bonded into the electrode paddle, the lead (when desired) can be pulled upward, with or without surrounding strain relief material, to emerge from the top surface of the paddle at an angle or curve to such top surface. This allows the base of the paddle to engage a bony opening, such as when the electrode is inserted into a patient's spine, skull, plane of fascia, etc.

11 Claims, 2 Drawing Sheets

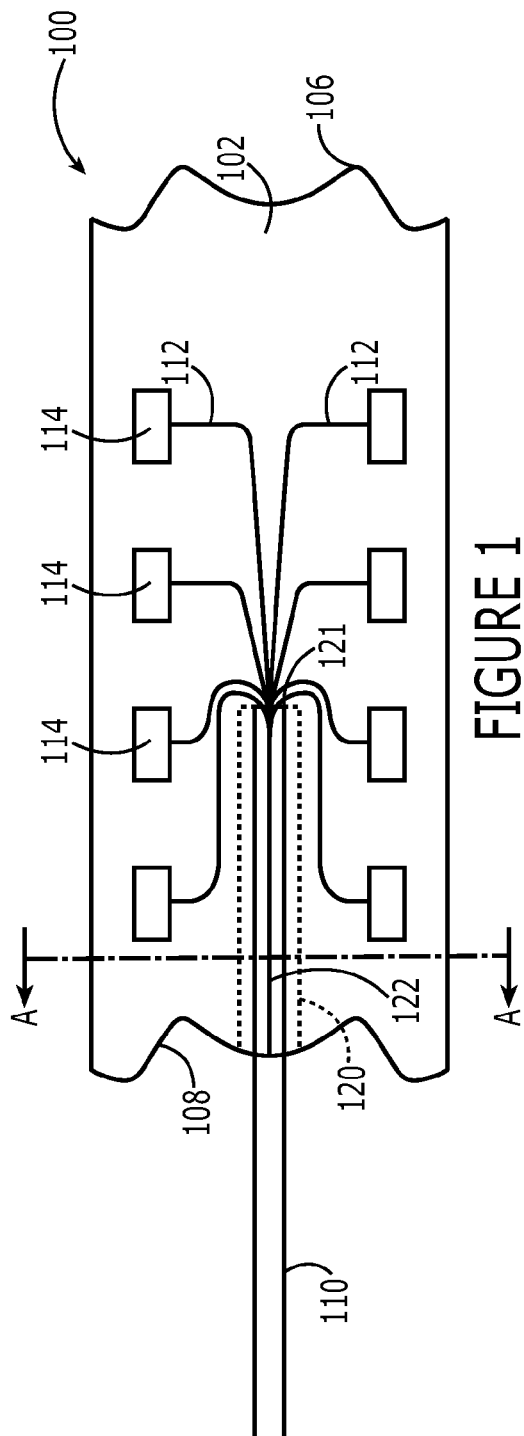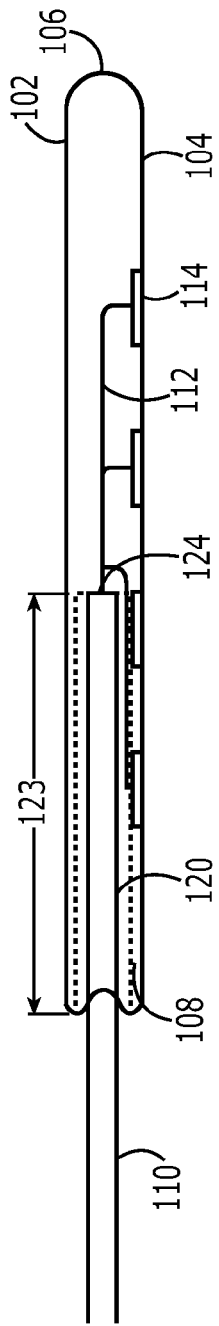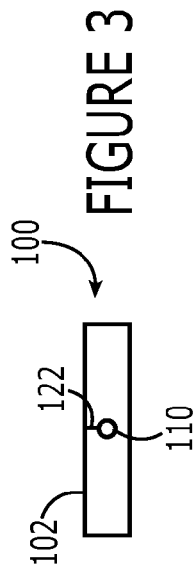

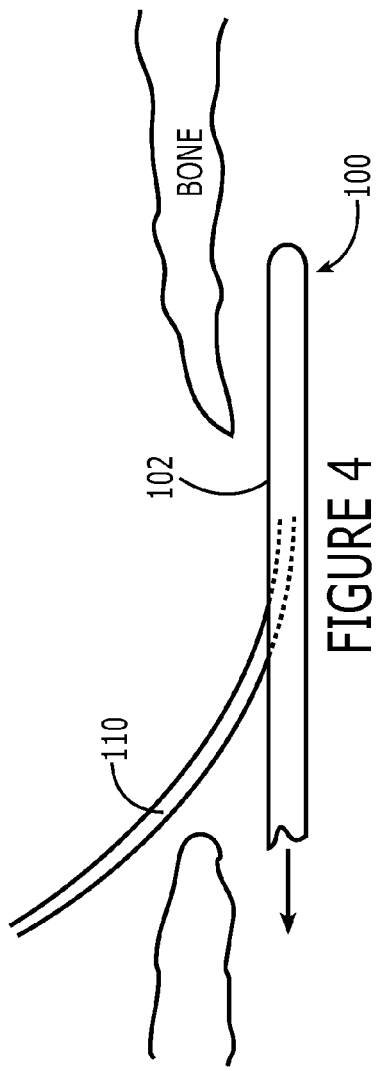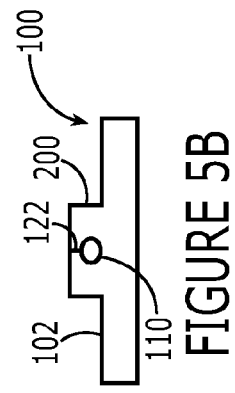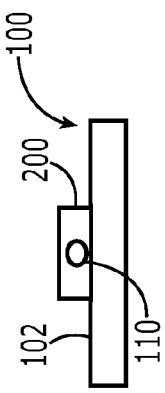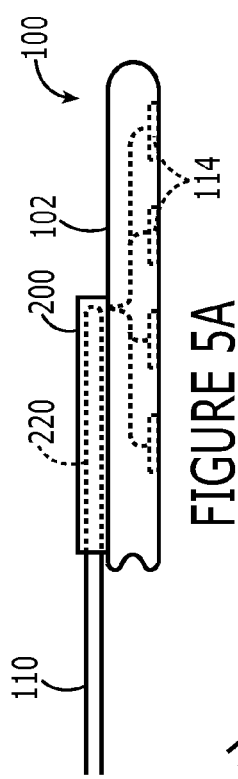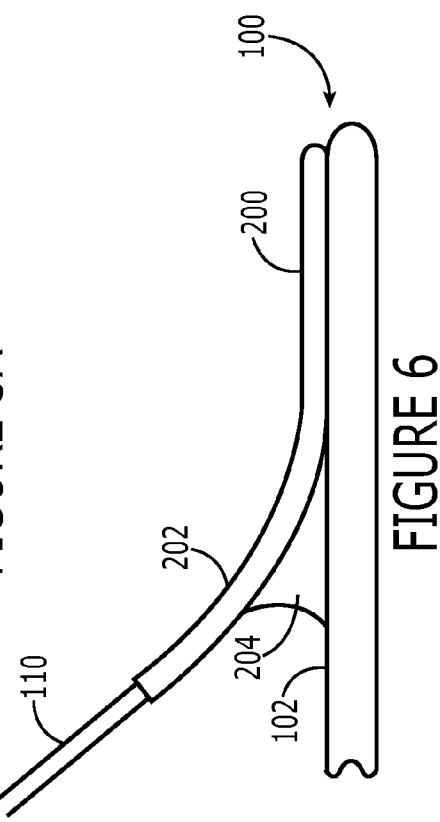

ELECTRODE HAVING ERECTABLE LEAD

CROSS REFERENCE TO RELATED APPLICATION

This application is a divisional of U.S. patent application Ser. No. 12/804,560 entitled "Electrode Having Erectable Lead," filed with the U.S. Patent and Trademark Office on Jul. 23, 2010 (now U.S. Pat. No. 8,676,346 issued Mar. 18, 2014), which application is based upon and claims benefit of U.S. Provisional Patent Application Ser. No. 61/228,399 entitled "Electrode Having Erectable Lead", filed with the U.S. Patent and Trademark Office on Jul. 24, 2009 by the inventor herein, the specification of which is incorporated herein by reference.

FIELD OF THE INVENTION

The present invention relates generally to the field of implantable medical electronic devices, such as electrical stimulators, epidural electrodes, defibrillators and pacemakers, and more particularly to an electrode having an emerging lead capable of being erected away from the plane of the electrode.

BACKGROUND OF THE INVENTION

Many humans (and other mammals and animals) receive benefit from implantable medical devices that deliver electrical pulses to or record from desired locations within their bodies. Such medical devices may comprise, for instance, spinal cord stimulation ("SCS") electrodes which typically comprise a small lead wire that is connected at one end to a power source and at the opposite end to a plurality of electrical contacts configured to transfer an electrical signal to the tissues that are to be stimulated. Those electrical contacts may, for instance, be situated in a paddle configured for implantation in a patient adjacent the tissue that is to be stimulated, such as along the spinal cord of a patient. SCS paddles typically have the lead wire or wires emerging from the bottom edge of the paddle, in the same plane as the body of the paddle. Also, typically there is a strain relief, molded along with the paddle, which surrounds the emerging lead or leads for approximately 5-8 mm, and beyond that the flexible leads continue onward to the power source.

SCS paddles provided with such coplanar strain relief and lead assemblies can provide certain advantages. For instance, such assembly can be advanced through an opening in the spinal canal (i.e., a laminectomy) upward or downward until the paddle and even the strain relief and a portion of the lead disappear from view. This can be useful in mapping stimulating contact positions higher or lower in the spinal canal than would be allowed by the length of the paddle alone. Moreover, molding and overall manufacturing are more easily accomplished for such configurations.

Unfortunately, however, such coplanar configurations also carry significant disadvantages. The placement of such components can be quite challenging, as the health care provider must specifically place the electrical contacts so that, when energized, they will record from or stimulate only the intended tissue, but not other tissue (stimulation of which in turn may cause perceived paresthesia, muscle contractions or even pain beyond that for which the patient originally sought treatment). In the case of traditional paddle electrode configurations, the emerging lead wire and strain relief must be bent as they emerge through an opening in bone, fascia or other tissue (for instance, laminectomy in the spine or burr hole in the skull), and to the extent that they are elastic, this introduces a bending moment, which tends to make the paddle migrate to one side or the other. Such migration will typically require surgical revision to replace the paddle in the proper position. Moreover, the techniques used to anchor such electrodes in place inside of the patient are insecure, such that the electrodes have a tendency to migrate away from the site at which they are originally implanted in the patient, at times in response to normal body movement of the patient. To the extent that it might not be anchored securely and can migrate downward, the lowermost part of a traditionally configured paddle electrode can come up and out of the spinal canal or skull, such that this part is no longer useful. Still further, during implantation, it can be quite difficult to engage a traditionally configured paddle electrode with the bony window formed by the laminectomy or burr hole, so as to mechanically lock the paddle in place within the epidural space of the spine or intracranially.

Attempts have previously been made to provide a paddle electrode in which the lead attaches to and emerges from the paddle along a face of the paddle, in turn reducing, at least to some extent, the bending moments that might be applied to the paddle from the lead. However, such prior efforts have themselves carried disadvantages, in that they prevent passage of the portion of the paddle at which the lead attaches above or below the bony window created by the laminectomy, because the nearly perpendicular emerging lead wire blocks further progress as it runs into the bony edge.

It would therefore be beneficial to provide an electrode that is more easily implanted by the health care provider in the intended position, and that is less prone to migration from the intended implantation site than previously known electrodes.

SUMMARY OF THE INVENTION

Disclosed is an electrode, such as an SCS paddle electrode, having a lead attached thereto along an interior portion of the electrode. The lead and electrode are configured such that the lead may be positioned generally coplanar with a top surface of the electrode, and may likewise be erected from such coplanar orientation up and away from the top surface of the electrode. Thus, the lead can maintain the typical configuration of emerging from the back end of the electrode, but because at least portions of the lead are not permanently bonded into the electrode paddle, the lead (when desired) can be pulled upward, with or without surrounding strain relief material, to emerge from the top surface of the paddle at an angle or curve to such top surface. This allows the base of the paddle to engage a bony opening, such as when the electrode is inserted into a patient's spine, skull, plane of fascia, etc.

With respect to a particularly preferred embodiment of the invention, an implantable electrode is provided comprising an electrode body having a front end, a back end, a top surface, and a bottom surface, and a lead having an electrode engaging portion extending into said electrode body from the back end and fixed to the electrode body at least at a lead terminal point located between the front end and the back end, wherein a section of said electrode engaging portion of said lead is erectable away from said top surface of said electrode.

BRIEF DESCRIPTION OF THE DRAWINGS

The numerous advantages of the present invention may be better understood by those skilled in the art by reference to the accompanying drawings in which:

FIG. 1 is a top view of an electrode according to one aspect of a particularly preferred embodiment of the invention.

FIG. 2 is a side, cross-sectional view of the electrode of FIG. 1.

FIG. 3 is a cross-sectional view along section line A-A of FIG. 1.

FIG. 4 is a side, perspective view of the electrode of FIG. 1 placed into a patient's spine.

FIGS. 5A and 5B are cross-sectional views of an electrode according to another aspect of the invention.

FIG. 6 is a side view of an electrode according to yet another aspect of the invention.

FIG. 7 is a cross-section view of the electrode of FIG. 6.

DETAILED DESCRIPTION OF THE INVENTION

The following description is of a particular embodiment of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

With regard to a particularly preferred embodiment of the invention, an implantable electrode is provided, such as a SCS paddle electrode, capable of being surgically implanted inside of a patient so as to transfer an electrical signal from a power source to targeted tissue in the patient. The paddle electrode is particularly configured so as to allow the lead wire to lie flat and generally coplanar with a surface of the paddle in those applications where a coplanar configuration is desired, but to likewise allow erection of the lead out of the plane of the paddle in those applications where an angled orientation between the lead and the paddle is desired.

With regard to a particularly preferred embodiment of the invention and with reference to FIGS. 1 and 2, a paddle electrode 100 is shown having a top surface 102, bottom surface 104, front end 106, and back end 108. A lead 110 enters the paddle electrode 100 through back end 108. Lead 110 contains a plurality of wires 112 that engage electrical contacts 114 situated on paddle electrode 100, and at an opposite end of lead 110 connect to a power source (not shown) so as to convey an electrical signal from such a power source to each of electrical contacts 114.

An electrode engaging portion 123 of lead 110 extends into paddle electrode 100 through a hollow channel 120, which electrode engaging portion 123 extends from back end 108 into a central portion of the body of paddle electrode 100, and terminating in such central portion of paddle electrode 100 at a lead terminal point 121. A longitudinal slit 122 likewise extends from back end 108 of paddle electrode 100 into such central portion, and extends downward into top surface 102 of paddle electrode 100 and into channel 120. Slit 122 thus provides an opening in top surface 102 of paddle electrode 100 through which lead 110 may be pulled, thus raising at least a section of electrode engaging portion 123 of lead 110 out of the plane of the top surface 102 of paddle electrode 100, while the forward-most end 124 of lead 110 (coinciding with lead terminal point 121) remains affixed to and generally parallel to the major axis of paddle electrode 100.

FIG. 3 provides a cross-sectional view along section line A-A of FIG. 1 of paddle electrode 100, in which it can be seen that slit 122 extends downward through top surface 102 of paddle electrode 100 and down to lead 110, thus allowing at least a section of electrode engaging portion 123 of lead 110 to be pulled upward and away from paddle electrode 100. Thus, when circumstances so dictate, the healthcare provider may pull the lead 110 upward so that a portion of lead 110 emerges from top surface 102 at an angle or a curve. As shown in FIG. 4, this allows the base of the paddle to mechanically engage a bony opening formed from a laminectomy procedure for purposes of inserting an electrode into a patient's spine. As those of ordinary skill in the art will appreciate, such application is not limited, however, to implantation of an electrode in a patient's spine, and may likewise be used for implantation of an electrode in a patient's skull, in a plane of fascia, subcutaneously, or in any other tissue.

With regard to another aspect of an embodiment of the invention and with particular reference to FIGS. 5A and 5B, paddle electrode 100 may be provided with a keel 200 positioned on top side 102 of paddle electrode 100. Once again, an electrode engaging portion of lead 110 extends into keel 200 through a hollow channel 220 in the same manner as described above. In this case, slit 122 may be provided extending downward from the top surface of keel 200 to lead 110, in turn allowing at least a section of the electrode engaging portion of lead 110 to be pulled upward and away from paddle electrode 100.

With regard to another aspect of an embodiment of the invention and with particular reference to FIGS. 6 and 7, paddle electrode 100 may again be provided a keel 200. Instead of a slit as shown in FIGS. 1-5, and while lead 110 extends into and is affixed to keel 200, a strain relief portion 202 of keel 200 is separable from the top surface 102 of paddle electrode 100. In this configuration, lead 110 may remain within the keel 200 as it separates from top surface 102 of paddle electrode 100, so that they might be erected together, with the portion 202 of keel 200 serving as strain relief.

A membrane may optionally be provided between keel 200 and top surface 102 of paddle electrode 100, which membrane maintains continuity between the lead 110 and the paddle electrode 100 when they diverge. The purpose of such web is to prevent tissue ingrowth which might make removal of the paddle electrode 100 more difficult once the patient's body encapsulates it in scar. Omitting this feature, on the other hand, would lead to greater tissue ingrowth and stability.

Optionally, adhesive may be used to bond lead 110 into paddle electrode 100 at or before the time of implantation, in the case that using it in the erected position is not contemplated. It is envisaged, however, that the above-described construction will be sufficiently secure, when lead 110 is simply engaged in paddle electrode 100, that this is not essential.

It shall be understood that various other characteristics of the novel erectable lead electrode of the current invention may be changed without departing from the scope and spirit of the present invention. For instance, the material composition of the paddle electrode may comprise any preferably chemically, electrically, and biologically inert material, such as medical grade, inert, elastomeric polymer or a silicone elastomer, or any other similarly configured flexible material suitable for surgical implantation and for use with electrical contacts 114. The material composition of the lead 110 may be similar to or different from that of the paddle electrode 100. In addition, while the exemplary embodiments show a paddle electrode of generally constant proportion and configuration throughout, it is contemplated that parts of the paddle electrode may include varying proportions or configurations.

It is believed that the present invention and many of its attendant advantages will be understood by the forgoing description. It is also believed that it will be apparent that various changes may be made in the form, construction and arrangement of the components thereof without departing from the spirit and scope of the invention or without sacrificing all of its material advantages. The form herein before described is merely an explanatory embodiment thereof.

I claim:

1. An implantable electrode comprising:
   an electrode paddle body having a front end, a back end, a top surface, and a bottom surface;
   a keel on the top surface of said electrode body; and
   a lead having an electrode engaging portion extending into said keel and affixed to said electrode paddle body, said electrode engaging portion of said lead extending into said keel from a back end of said keel adjacent the back end of said electrode paddle body and fixed to the electrode paddle body at a lead terminal point located between the front end and the back end of said electrode paddle body, wherein said electrode engaging portion is configured to sit entirely within the keel when in a first position;
   wherein a section of said electrode engaging portion of said lead is erectable away from said first position to a second position in which said section of said electrode engaging portion extends away from said electrode paddle body.

2. The implantable electrode of claim 1, further comprising a plurality of electrical contacts within one of said top surface and said bottom surface of said electrode, and a plurality of wires extending from said lead at said lead terminal point to said plurality of electrical contacts.

3. The implantable electrode of claim 1, wherein said lead terminal point is located at a point on said electrode body that is closer to a midpoint of said electrode body between said front end and said back end than to the back end of said electrode body.

4. The implantable electrode of claim 1, said keel further comprising an elongate strip positioned on said top surface of said electrode body and having a width less than a width of the top surface of said electrode body.

5. The implantable electrode of claim 4, wherein at least a portion of said keel is fixed to the top surface of said electrode body.

6. The implantable electrode of claim 1, wherein said lead extends into a hollow channel extending into said keel from the back end of said electrode body to said lead terminal point.

7. The implantable electrode of claim 6, said keel further comprising a longitudinal slit on a top surface of said keel extending from said top surface of said keel to said hollow channel.

8. The implantable electrode of claim 7, wherein said section of said electrode engaging portion of said lead is erectable outward from said hollow channel through said longitudinal slit and away from said top surface of said electrode body.

9. The implantable electrode of claim 6, wherein said keel is directly attached to said top surface of said electrode body along only a first portion of the length of said keel, and is not directly attached to said top surface of said electrode body along a second portion of the length of said keel.

10. The implantable electrode of claim 9, wherein said section of said electrode and said second portion of said keel are extendable away from said top surface of said electrode body.

11. The implantable electrode of claim 10, further comprising a membrane situated between said top surface of said electrode body and said second portion of said keel.

* * * * *